United States Patent
Hemming et al.

(10) Patent No.: US 11,318,038 B2
(45) Date of Patent: May 3, 2022

(54) ARM SUPPORT SYSTEM

(71) Applicants: Mark Hemming, Santa Ynez, CA (US); Bryan Bowman, Roann, IN (US)

(72) Inventors: Mark Hemming, Santa Ynez, CA (US); Bryan Bowman, Roann, IN (US)

( * ) Notice: Subject to any disclaimer, the term of this patent is extended or adjusted under 35 U.S.C. 154(b) by 75 days.

(21) Appl. No.: 16/686,142

(22) Filed: Nov. 16, 2019

(65) Prior Publication Data
US 2020/0337878 A1 Oct. 29, 2020

Related U.S. Application Data

(60) Provisional application No. 62/839,668, filed on Apr. 27, 2019.

(51) Int. Cl.
*A61F 5/37* (2006.01)

(52) U.S. Cl.
CPC .................. *A61F 5/3738* (2013.01)

(58) Field of Classification Search
CPC ...... A61F 5/3738; A61F 5/373; A61F 5/3761; A61F 5/3723; A44B 11/25
USPC ................................................ 24/303; 602/4
See application file for complete search history.

(56) References Cited

U.S. PATENT DOCUMENTS

| | | | | |
|---|---|---|---|---|
| 1,490,381 A | * | 4/1924 | Gobar | A61F 5/3738 602/4 |
| 1,808,422 A | * | 6/1931 | MacDonald | A61F 5/05808 602/4 |
| 2,358,551 A | * | 9/1944 | Beaton | A61F 5/0118 224/259 |
| 2,616,419 A | * | 11/1952 | Karfiol | A61F 5/3738 602/4 |
| 4,355,635 A | * | 10/1982 | Bihl | A61F 5/3738 128/DIG. 15 |
| 4,564,008 A | * | 1/1986 | Donahoo | A61F 5/3738 602/4 |
| 4,815,639 A | * | 3/1989 | Lehman | A47D 13/025 224/159 |
| 5,413,552 A | * | 5/1995 | Iwuala | A61F 5/3738 128/878 |
| 6,095,993 A | * | 8/2000 | Hawkins | A61F 5/3738 602/4 |
| 8,418,897 B1 | * | 4/2013 | Young | A61F 5/026 224/160 |
| 9,968,476 B2 | * | 5/2018 | Hatto | A61F 5/3738 |
| 2003/0135141 A1 | * | 7/2003 | Berhorst | A61F 5/3723 602/4 |
| 2016/0074205 A1 | * | 3/2016 | Yao | A61F 5/3738 602/4 |

* cited by examiner

*Primary Examiner* — Camtu T Nguyen
(74) *Attorney, Agent, or Firm* — Felix L. Fischer

(57) ABSTRACT

An arm support system incorporates a harness with a support plate engaged to the harness. The support plate has an engagement element. A wrist strap has a mating engagement element and the wrist strap is adapted to be engaged to a wrist of an injured arm. Engagement of the mating engagement element onto the engagement element supports the injured arm.

9 Claims, 14 Drawing Sheets

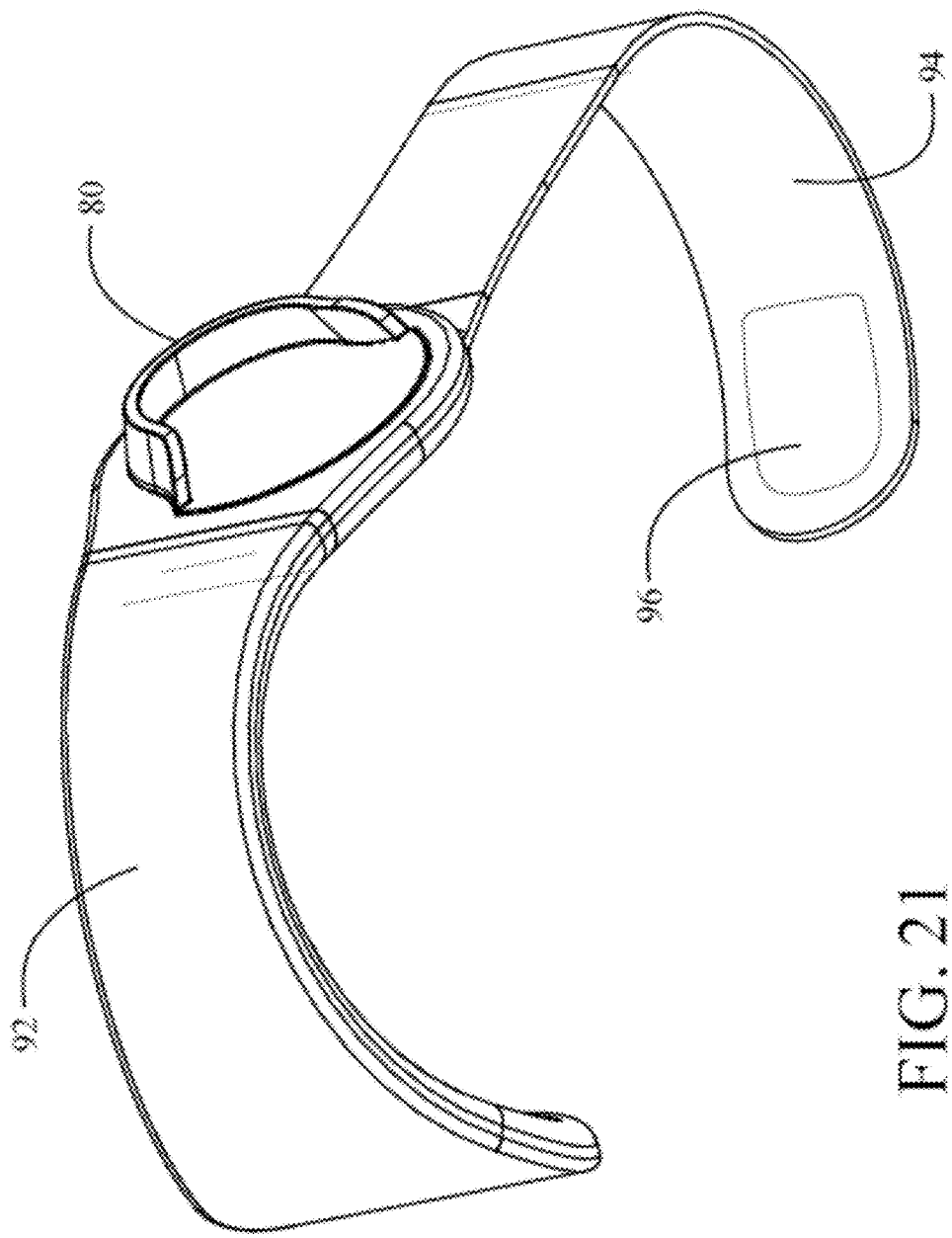

ARM SUPPORT SYSTEM

REFERENCE TO RELATED APPLICATIONS

This application claims priority of U.S. provisional application Ser. No. 62/839,668 entitled ARM SUPPORT SYSTEM filed on Apr. 27, 2019, the disclosure of which is incorporated herein by reference.

BACKGROUND INFORMATION

Field

The implementations disclosed herein relate generally to support devices for shoulder injury/surgery rehabilitation and, more particularly to an arm support system having a shoulder harness with associated straps engaged to a support plate adapted to removably connect an attachment device mounted on a wrist strap.

Background

Shoulder injuries often require surgery and rehabilitation which necessitate the use of a brace to support the arm associated with the injured shoulder. In early recovery devices such as the Adaptive Arm Support System disclosed in U.S. Pat. No. 9,205,017 or the Shoulder Sling with Support Pillow and Pouch disclosed in U.S. Pat. No. 7,563,236 are employed to fully immobilize the arm and shoulder. As recovery progresses, standard arm sling supports such as the Device for Stabilizing an Arm disclosed in US patent publication 2006/0258966 or the Shoulder Orthosis having a Supportive Strapping System disclosed in US patent publication 2012/0209159 may be employed. However, all of these devices significantly restrict the use of the recovering arm. To use the arm, the sling must be substantially removed or unattached. In many late stage recovery situations, the arm may be usable in most instances but temporary support to rest the should or relieve pain is desirable.

SUMMARY

The implementations disclosed herein provide an arm support system employing a harness with a support plate engaged to the harness to be positioned on the chest of a user. The support plate has an engagement element. A wrist strap has a mating engagement element and the wrist strap is adapted to be engaged to a wrist of an injured arm of the user. Engagement of the mating engagement element onto the engagement element supports the injured arm.

DETAILED DESCRIPTION

Figure 1:
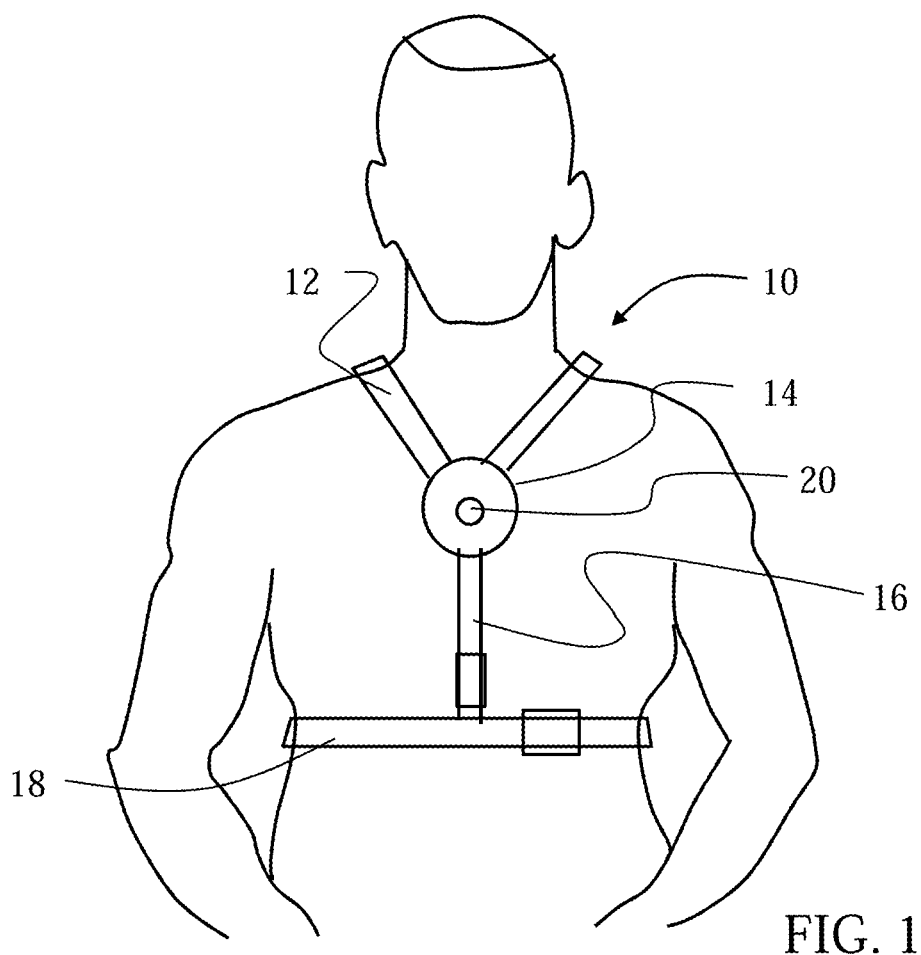
FIG. 1 is a front view of a first implementation of the arm support system with a neck harness.
Figure 2:
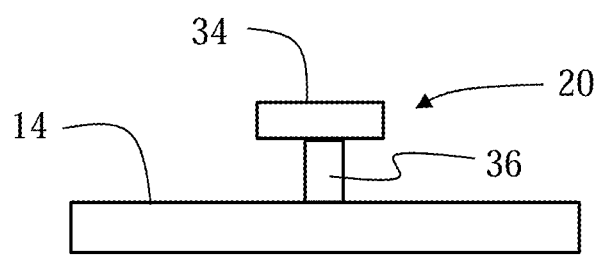
FIG. 2 is a side view of a first implementation of the engagement element.
Figure 3:
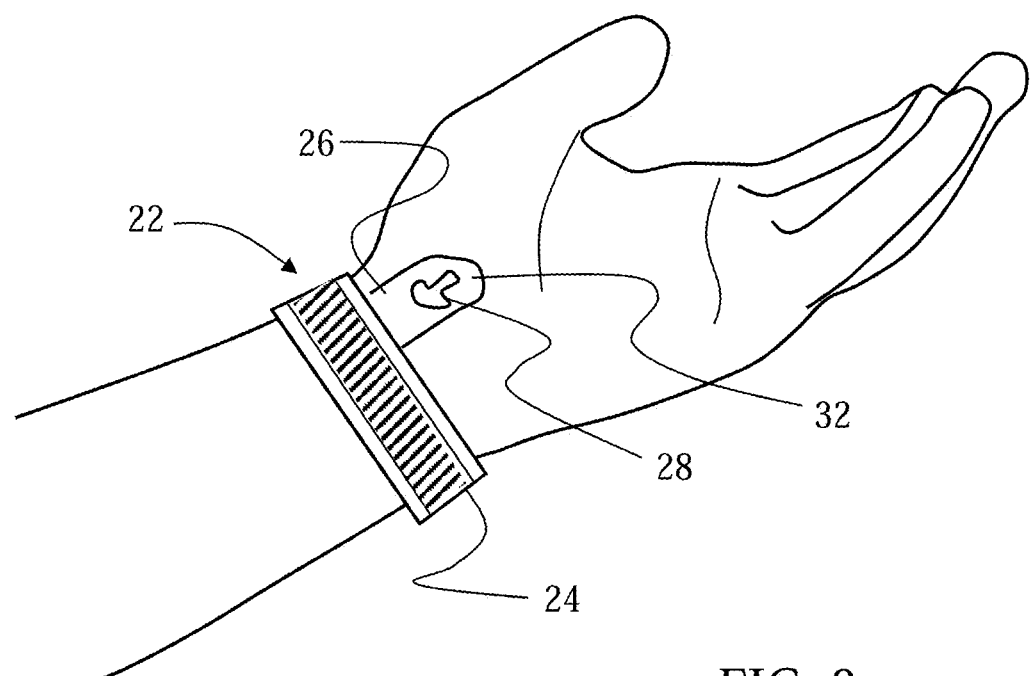
FIG. 3 is a pictorial representation of the wrist strap of the arm assembly with a first implementation of the mating engagement element.
Figure 4:
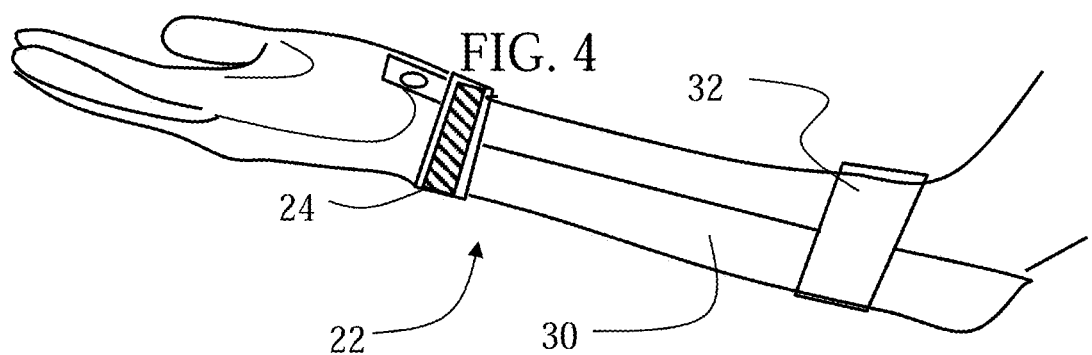
FIG. 4 is a pictorial representation of the arm assembly with optional forearm and elbow cup support.

As seen in the drawings, the Arm Support System incorporates a harness 10 engaged to a support plate 14 on the chest proximate the sternum or slightly beyond the sternum distal from the injured shoulder. In a first implementation as seen in FIG. 1, upper strap elements 12 extend from the support plate 14 surrounding the neck and a chest strap 16 extends downward from the support plate to engage a waist strap 18. The upper strap elements may encircle the neck and meet or may extend over the shoulders and engage the waist strap at the back. The support plate 14 incorporates an engagement element 20. In the first implementation as shown in FIG. 2, the engagement element 20 has a clip 21 which may be a circular button, a hook or other device, as will be described in greater detail subsequently. An arm assembly 22 worn on the wrist of the injured arm includes a wrist strap 24 encircling the wrist and an engagement tab 26 extending from the wrist strap which incorporates a mating engagement element 28 to be attached to the engagement element 20. In the first implementation as shown in FIG. 3, the mating engagement element 28 is a slotted aperture 32 The arm assembly 22 may also optionally include a forearm and elbow cup 30 extending from the wrist strap 24 and a support band 33 proximate the elbow for securing the forearm and elbow cup 30 as shown in FIG. 4.

Figure 5:
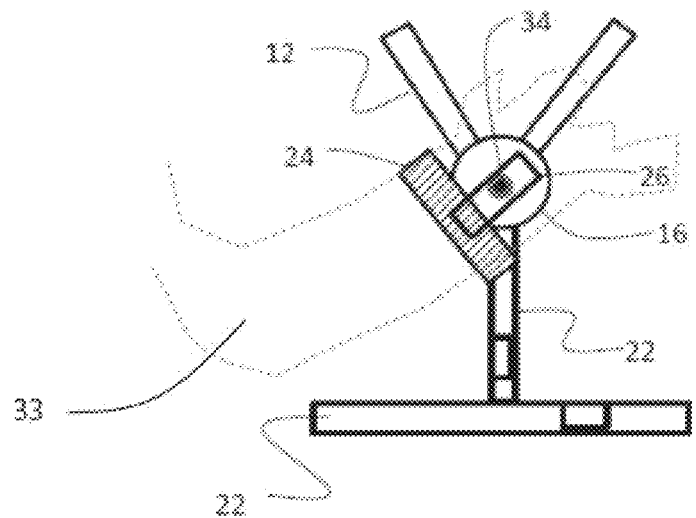
FIG. 5 is a depiction of attachment of the mating engagement element to the engagement element to support the arm.

In the first implementation as shown in FIG. 5, for engagement to support the arm depending from the injured shoulder (referred to herein as the "injured arm"), the injured arm 33 is bent and the slotted aperture 32 is engaged on the extending clip 21. As shown in the drawings, the aperture 28 may be tapered or have a slot to be restrained by a plate 34 on the distal end of the extending clip 21 with the slot receiving a rod 36 of the clip. Removable attachment of the mating engagement element 28 to the engagement element 20 allows the injured arm to be supported from the wrist and drape across the chest with the upper arm of the injured shoulder depending substantially vertically offsetting any load of the lower arm and supporting the arm to relieve the shoulder. Disconnecting the mating engagement element from the engagement element by removing the engagement tab from the clip allows free use of the arm. Connection and disconnection of the engagement tab and clip avoids any requirement for unhooking straps or removing a sling to allow use of the arm while easily allowing reattachment to provide support for the arm whenever necessary.

Figure 6:
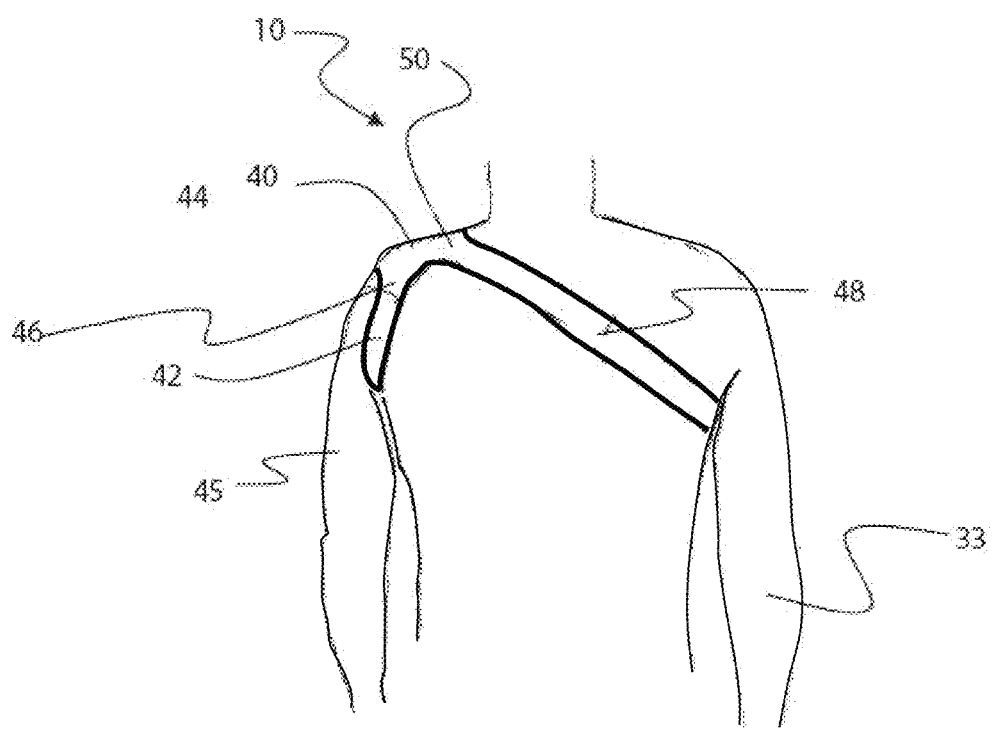
FIG. 6 is a back view of a second implementation of the harness.
Figure 7:
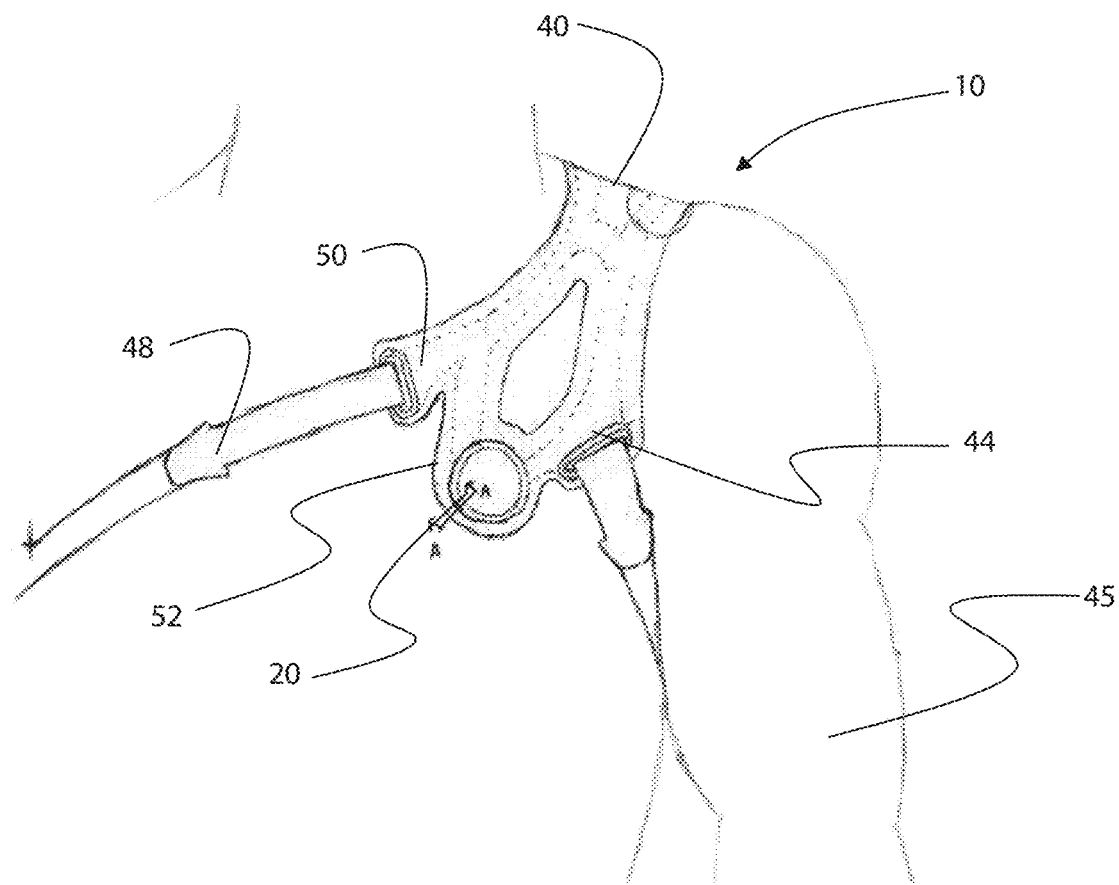
FIG. 7 is a front view of the second implementation of the harness.
Figure 8:
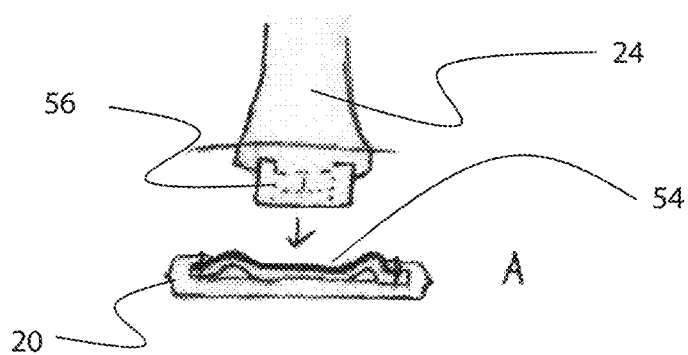
FIG. 8 is a side partial section view of the magnetic mating engagement element and engagement element of a second implementation of engagement system.

A second implementation of the harness 10 is shown in FIGS. 6 and 7. The harness 10 incorporates a shoulder pad 40 which is received on the trapezius muscle between the neck and deltoid muscle. An under-arm strap 42 extends from a front lower lateral tab 44 on the shoulder pad under the uninured arm 45, encircling the arm and engaging a rear lower tab 46 on the shoulder pad. A chest strap 48 extends from a posterior mid tab 50 on the shoulder pad and extends under the injured arm 33 encircling the chest and engages an anterior lower medial tab 51 on the shoulder pad. The engagement element 20 is supported on a bottom tab 52 extending from the shoulder pad acting as the support plate. The arrangement of the shoulder pad, arm strap and chest strap avoids any uncomfortable pressure on the user's neck.

The engagement element 20 in the second implementation is a first magnetic element 54. A second magnetic element 56 on the wrist strap 24, acting as the mating engagement element 28, magnetically attaches to the first magnetic element when brought into close proximity thereby removably attaching the wrist strap and wrist of the injured arm to the bottom tab 52 of the chest strap. This allows the arm to be supported from the wrist, as in the first implementation, and drape across the chest with the upper arm of the injured shoulder depending substantially vertically but without the load of the lower arm. Disconnection of the second magnetic element 56 from the first magnetic element releases the wrist allowing the injured arm to be freely used.

Figure 9:
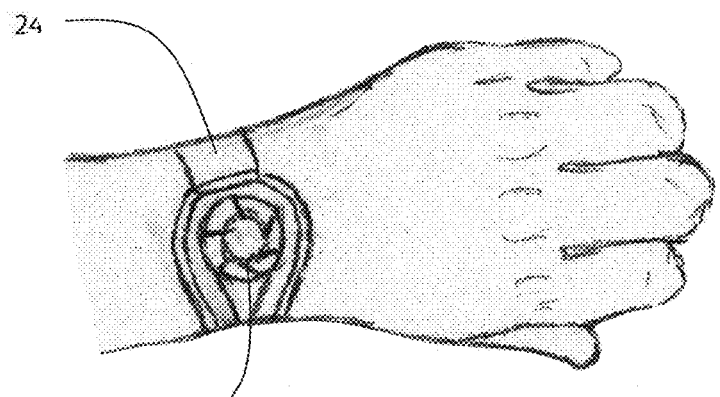
FIG. 9 is a top view of the wrist strap and control element of the second implementation of the engagement system.
Figure 10:
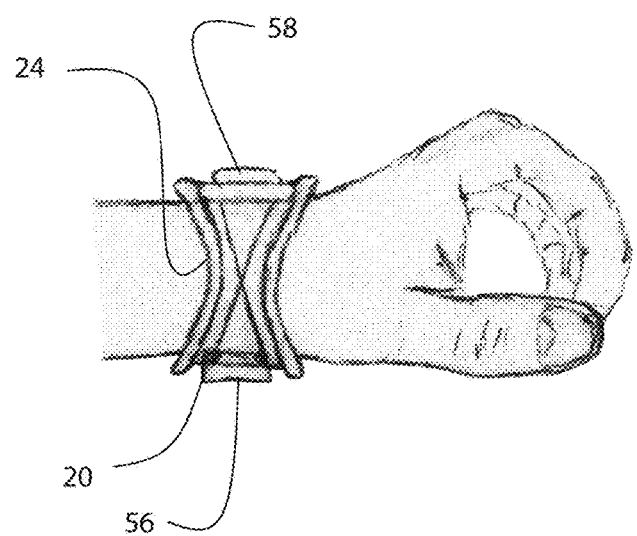
FIG. 10 is a side view of the wrist strap and control element.
Figure 11A:
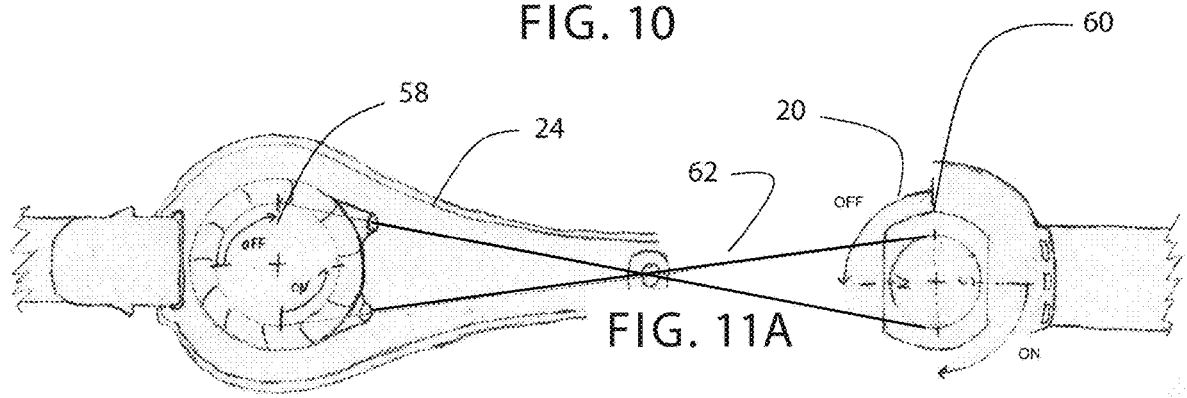
FIG. 11A is a partial segmented view of the wrist strap and control element.
Figure 11B:
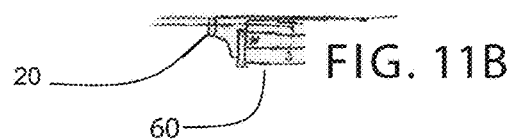
FIG. 11B is a section view of the rotatable magnetic element.
Figure 12:
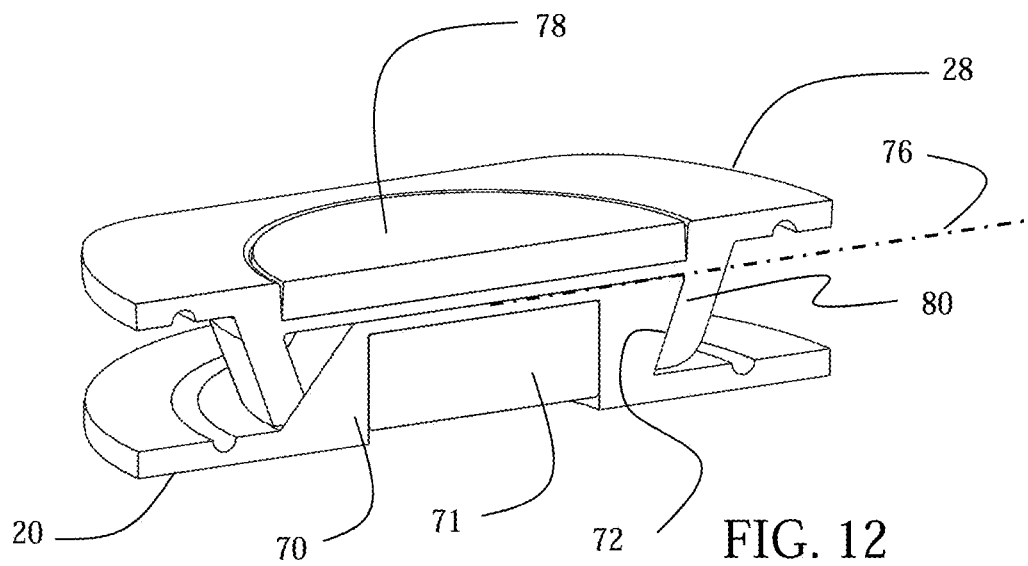
FIG. 12 is a section view of a third implementation of the engagement system.
Figure 13:
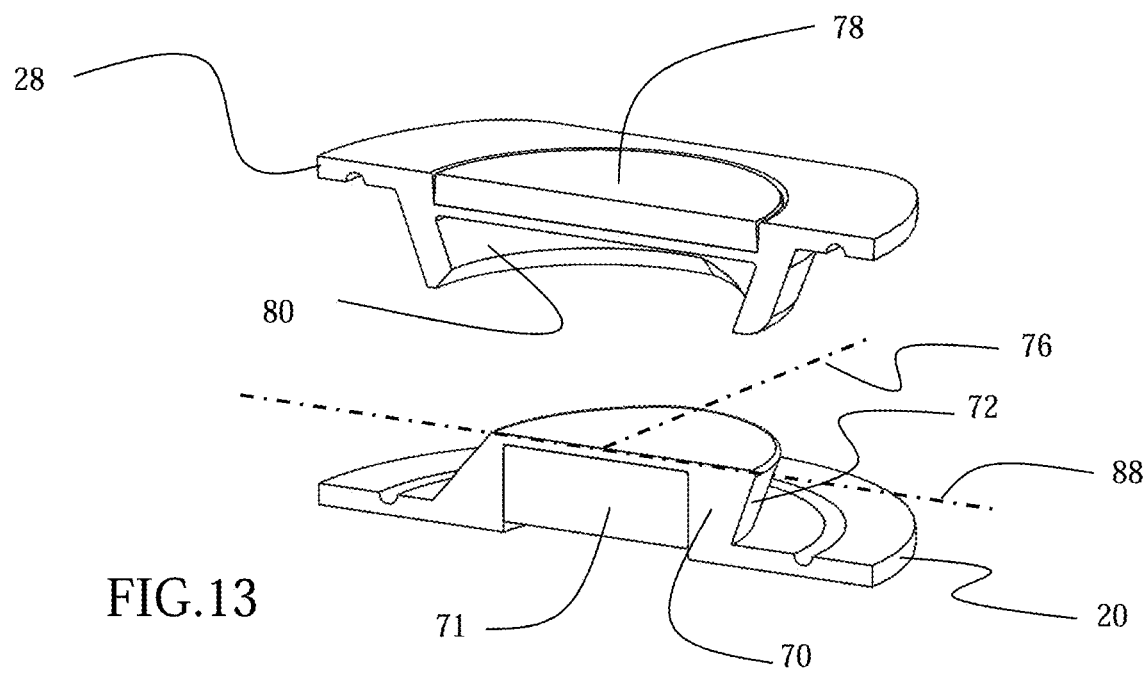
FIG. 13 is an exploded view of the third implementation of the engagement system.
Figure 14:
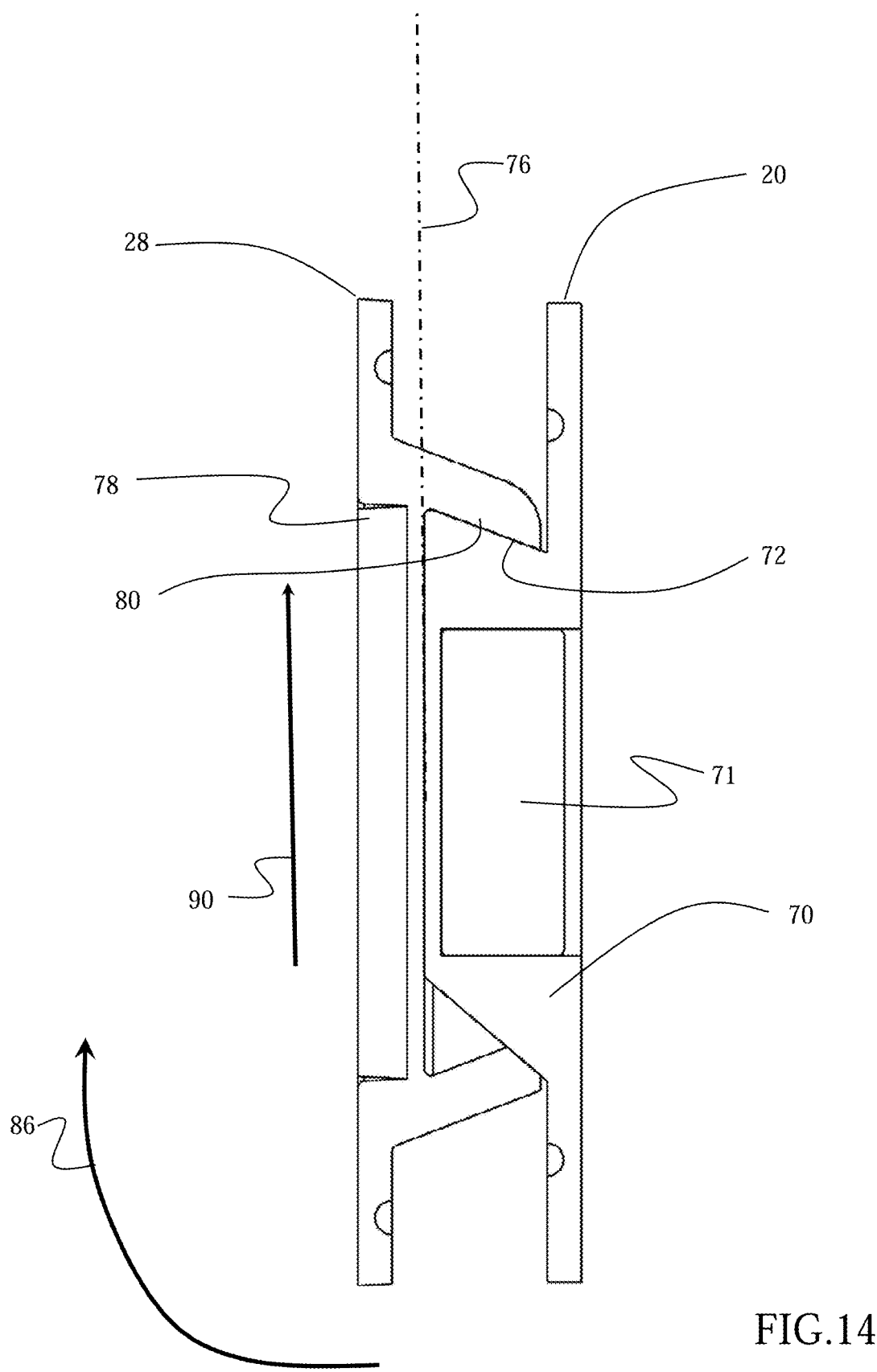
FIG. 14 is a side section view of the third implementation of the engagement system.
Figure 15:
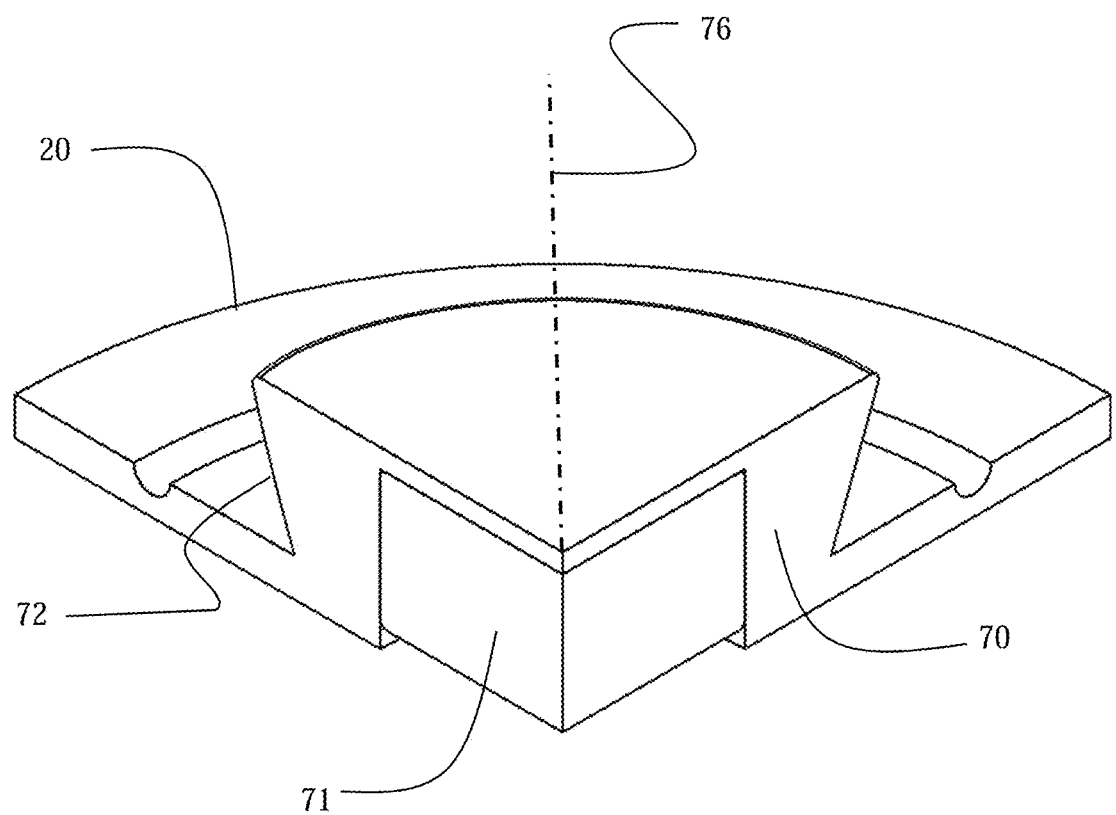
FIG. 15 is a double section segment of the engagement element of the third implementation of the engagement system.
Figure 16:
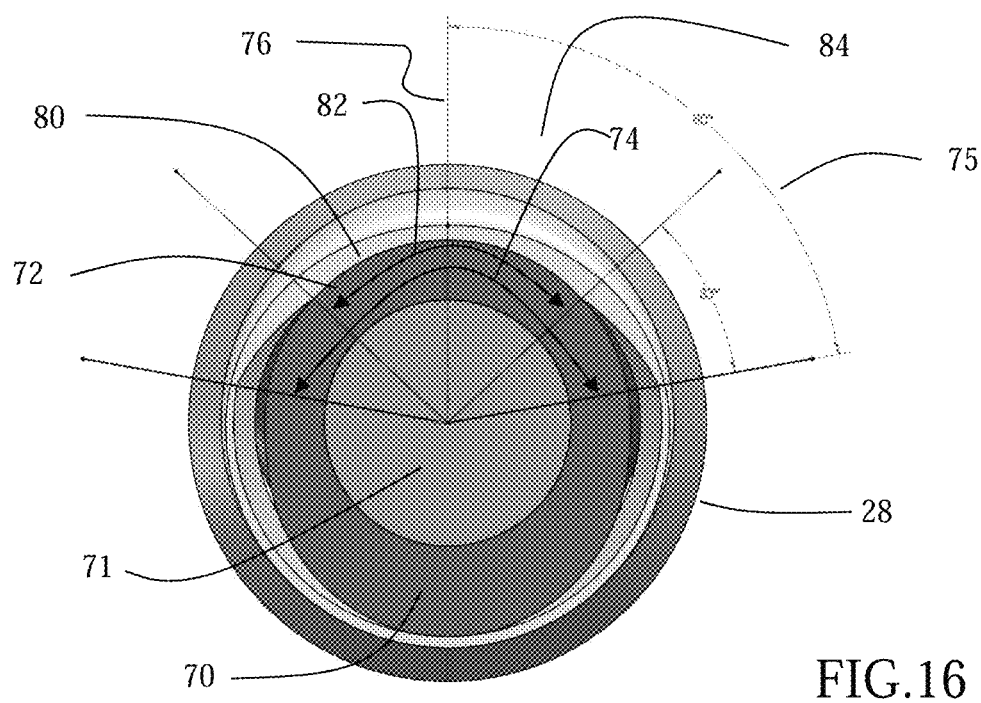
FIG. 16 is a rear-view representation of the engaging interlock of the female mating engagement element and the male engagement element of the engagement system.
Figure 17:
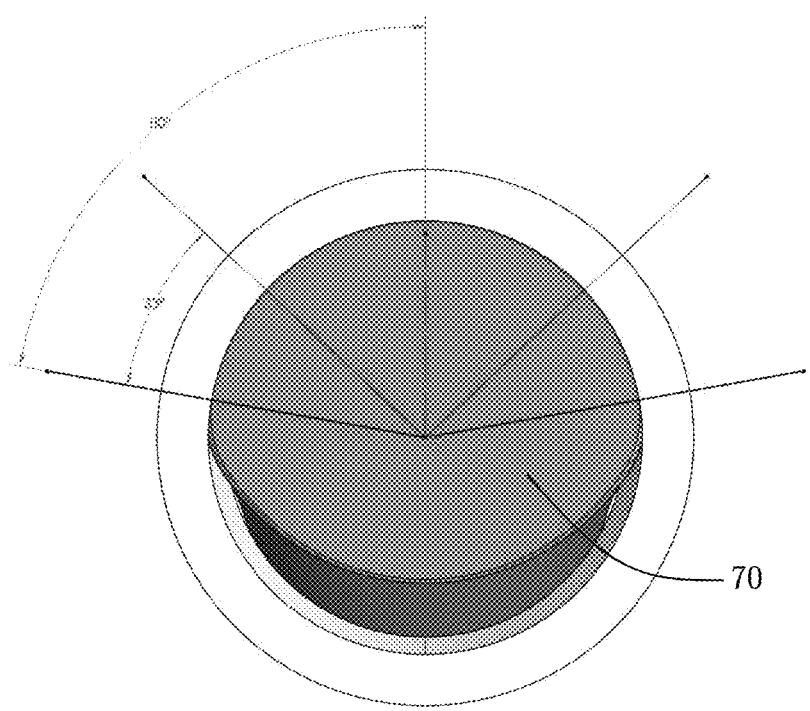
FIG. 17 is a front view of the male engagement element.

As seen in FIGS. 9 and 10 the second magnetic element 56 of the second implementation of the engagement system is a switchable magnet allowing the magnetic force to be eliminated or reduced for easy separation from the first magnetic element 54. A rotating switch 58 is provided on the dorsal side of the wrist strap 24. The switch 58 is engaged to a wrist magnet 60 in the second magnetic element, located on the palmer side of the wrist, to rotate the wrist magnet 60 from an attraction orientation to a neutral or repelling orientation with respect to the first magnetic element 54. As seen in FIGS. 11A and 11B the implementation of the switch operation employs fine plastic-coated cables 62 engaged around the wrist magnet 60 pivotally mounted to act as a pulley. Rotation of the switch 58 causes rotation of the wrist magnet 60 to alter the orientation of the poles of the magnet. First magnetic element 54 may be a mating magnet 64 with north and south poles oriented in a first azimuthal position on the bottom tab 52, nominally vertically. In an active or securing position, the wrist magnet 60 has an orientation defined such that placement of the wrist of the injured arm with the wrist strap in place proximate the engagement element 20 matches the first azimuthal position with opposing polarity of the mating magnet 64 and wrist magnet 60. Engagement to support the injured arm is then accomplished by merely placing the wrist strap and wrist magnet 60 in close proximity to the engagement element. With the wrist strap (and wrist and injured arm) attached to the engagement element 20, disconnection is accomplished by rotating the switch 58 with the hand of the uninjured arm thereby altering the polarity of the wrist magnet 60 as shown in FIGS. 11A and 11B, to release the magnetic attraction with the mating magnet.

A third implementation of the engagement system is shown in FIGS. 12-17. Employing magnetic attraction for easy engagement of the wrist strap with the mating engagement element to the engagement element on the harness is desirable. However, supplementing the hanging force reaction capability of the engagement system without magnetic elements of sufficient strength to magnetically support the injured arm alone and to facilitate easy release of the engagement system is accomplished with a magnetic male tab 70 acting as the engagement element 20 extending from the bottom tab 52 of the support pad of the harness. In the example for the third implementations, the tab 70 employs a disc magnet 71 embedded in formed plastic with the desired structural support shape. The tab 70 incorporates a conical lip segment 72 extending over an engagement arc 74 having a sector angle 75 spanning a vertical axis 76. For the exemplary implementation, the sector angle 75 is 80° on either side of the axis. The mating engagement element 28 incorporates a magnetic metal disc 78 embedded or constrained within a mating modified conical lip segment 80 spanning the vertical axis 76 with a mating engagement arc 82 have a second sector angle 84 less than the sector angle 75. The mating modified conical lip segment mating is concentrically received over the conical lip segment 72 of the tab 70. For the exemplary implementation, the second sector angle is 47° on either side of the vertical axis 76. The mating modified conical lip segment 80 (best seen in FIG. 13) engages the conical lip segment 72 providing vertical force reaction for the wrist strap supporting the injured arm. However, slight rotation represented by arrow 86 (retroversion) in FIG. 14 about an anterior orthogonal rotation axis 88 (seen in FIG. 13) breaks the magnetic attraction between the disc magnet 71 and magnetic metal disc 78 and slight upward movement as represented by arrow 90 allows the wrist strap to be easily disconnected from the engagement element. The relative overlap of the engagement arc 74 and mating engagement arc 82 allows rotation of the mating engagement element relative 28 to the tab 70 while still maintaining contact of the mating modified conical lip segment 80 on the conical lip segment 72. For the exemplary implementation a 33° rotation in either direction is allowable.

Engagement of the mating engagement element 28 to the tab 70 is accomplished by positioning the wrist strap and mating engagement element 28 slightly above and proximate the tab 70. With a slight downward motion of the wrist, the magnetic attraction of disc magnet 71 and magnetic metal disc 78 urges the mating engagement element into contact and further downward motion of the wrist engages the mating modified conical lip segment 80 onto the conical lip segment 72 of the tab 70 to support the injured arm. Removal of the wrist strap 24 and mating engagement element 28 is accomplished by slight retroversion of the wrist, assisted by the hand of the uninjured arm if necessary, to break the magnetic attraction between the disc magnet 71 and magnetic metal disc 78 and slight upward movement as represented by arrow 90 to disconnected from the engagement element.

Figure 18:
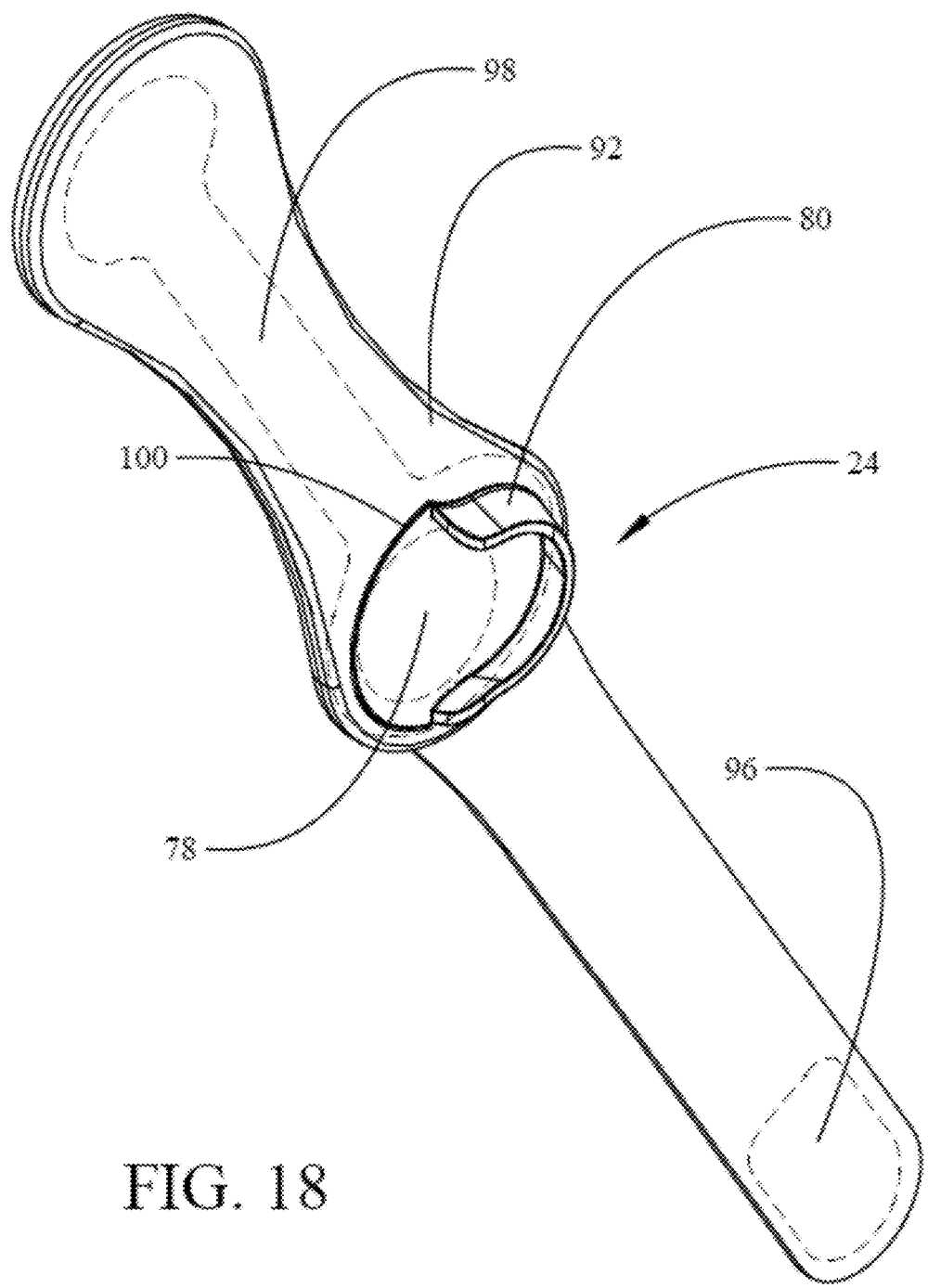
FIG. 18 is a pictorial view of a wrist strap employing the third implementation of the engagement system.

A wrist strap 24 for use with the third implementation of the engagement system is shown in FIG. 18. The mating modified conical lip segment 80 is embedded in a pliable wrist support element 92 extending through an aperture 100. A pliable wrap 94 wraps around the wrist to be engaged to the pliable wrist support element 92 with a hook element 96 of a hook and loop fastener. The pliable wrist support element 92 may have a covering acting as the loop element or a loop strip for adjustable attachment of the hook element 96. A bendable spade element 98 is carried within the pliable wrist support element 92.

Figure 19:
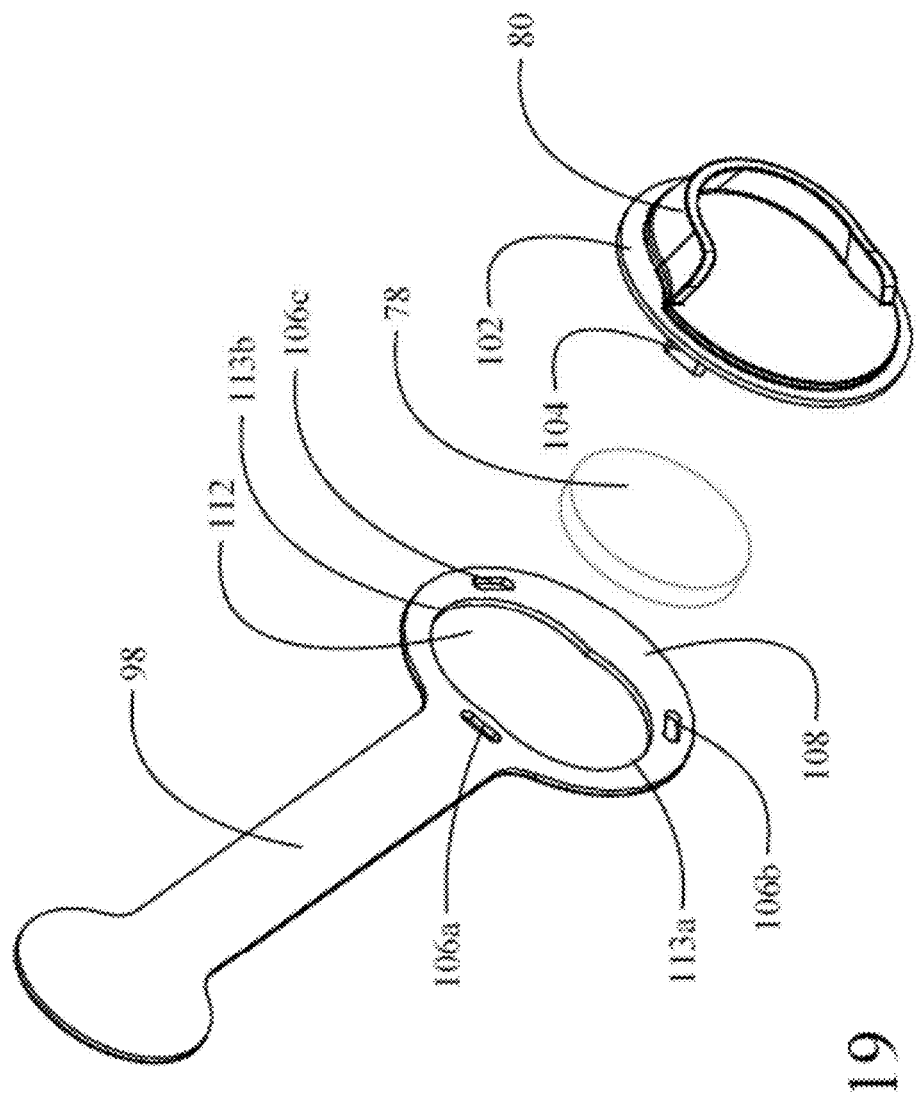
FIG. 19 is an exploded view of structural elements of the wrist strap of FIG. 18.
Figure 20A:
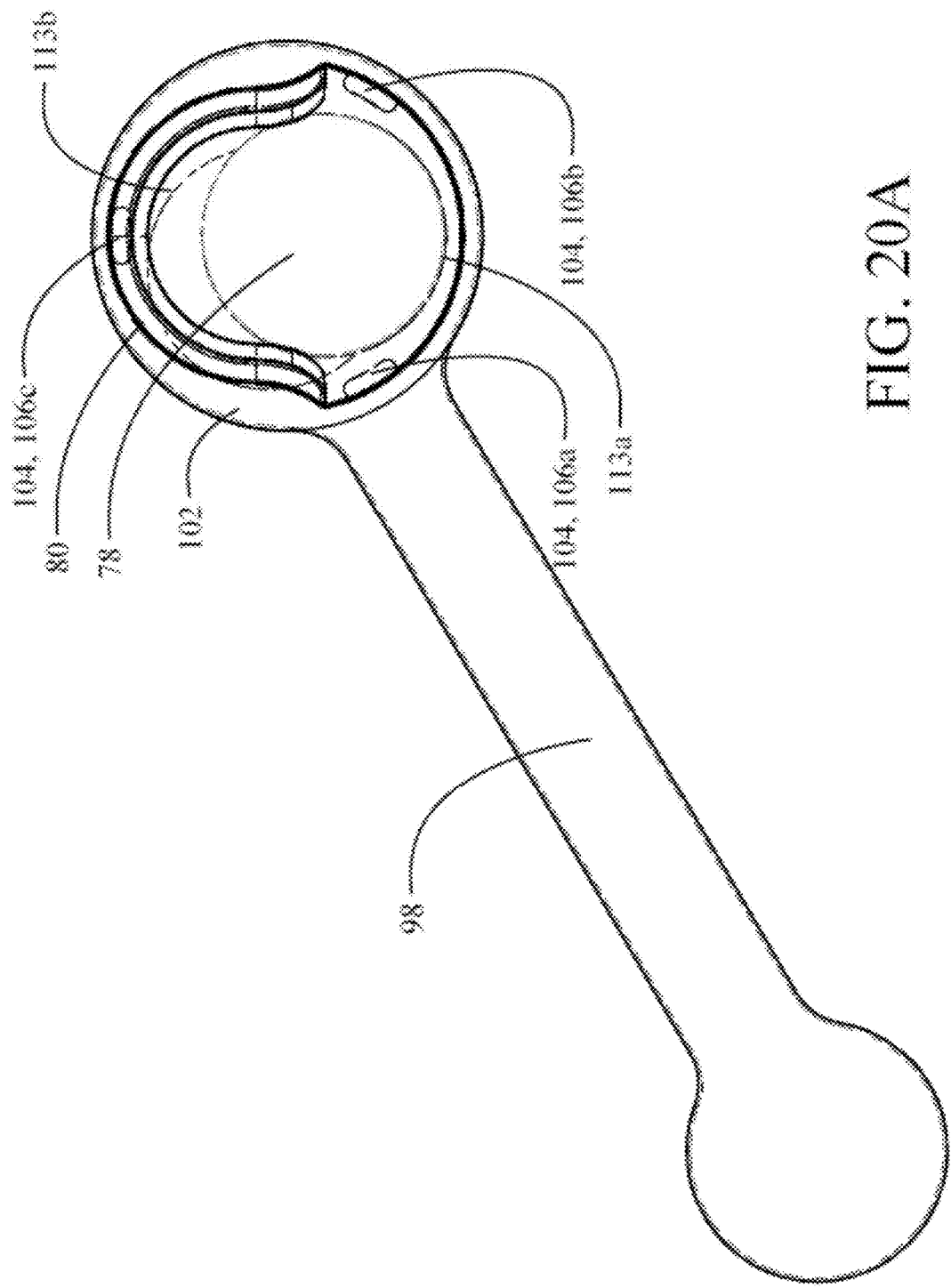
FIG. 20A is a view of the wrist strap of FIG. 18 configured for left handed support.
Figure 20B:
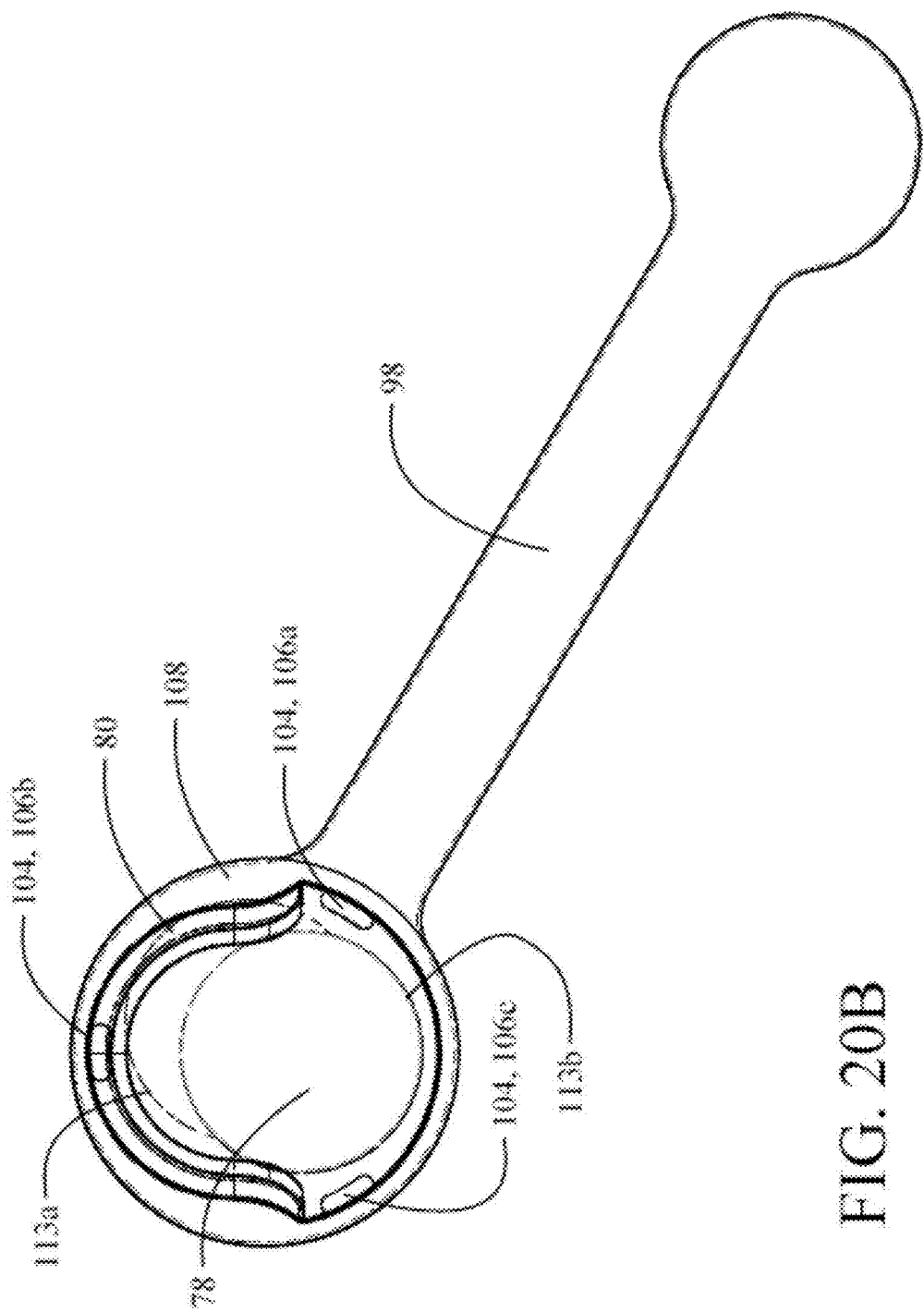
FIG. 20B is a view of the wrist strap of FIG. 18 configured for right handed support; and, FIG. 21 is a pictorial view of the wrist strap of FIG. 18 with the spade element bent and the flexible tab partially flexed

As seen in FIG. 19, the spade element 98, magnetic metal disc 78 and the mating modified conical lip segment 80 are supported in the pliable wrist support element 92. The mating modified conical lip segment 80 extends through the aperture 100 (as seen in FIG. 18) from a flange 102 constrained by the circumference of the aperture. The flange 102 has a plurality of protruding tabs 104 which are selectively received in a plurality of mating holes 106a-106c in a base 108 of the spade element 98. Selection of clocking of the flange 102 and the protruding tabs 104 with respect to the mating holes 106a-106c allows selection of support for the left wrist and arm as shown in FIG. 20A or the right wrist and arm as shown in FIG. 20B. The mating magnetic disc 78 is constrained in the pliable wrist support element 92 positioned within an inner circumference 110 of the flange 102 for engagement with the disc magnet 71 as previously described. An oblong aperture 112 with intersecting circular circumferences 113a and 113b in the base 108 of the spade element 98 assists in positioning and constraining the mating magnetic disc 78 with placement of the mating magnetic disc within circumference 113a with mating modified conical lip segment 80 and flange 102 clocked for left wrist support and within circumference 113b with mating modified conical lip segment 80 and flange 102 clocked for right wrist support.

The spade element 98 is deformable to wrap around the wrist with the pliable wrist support element 92 forming a padded support element engaging the ulnar aspect of the wrist to react the weight of the wrist and arm when supported from the mating modified conical lip segment 80 as seen in FIG. 21 with the spade element 98 deformed and pliable wrap 94 partially wrapped for interconnection.

Having now described various implementations in detail as required by the patent statutes, those skilled in the art will recognize modifications and substitutions to the specific implementations disclosed herein. Such modifications are within the scope and intent of the present invention as defined in the following claims. Within the specification and the claims, the terms "comprising", "incorporate", "incorporates" or "incorporating", "include", "includes" or "including", "has", "have" or "having", and "contain", "contains" or "containing" are intended to be open recitations and additional or equivalent elements may be present. As used herein the terms "right" and "left" are employed to describe relative positioning and other than for the specific implementations disclosed may be substituted with appropriate descriptors such as "first" and "second", "top" and "bottom" or "upper" and "lower" depending actual orientation of the implementation.

What is claimed is:

1. An arm support system comprising:
    a harness;
    a support plate engaged to the harness adapted to be positioned on a chest of a user, the support plate having an engagement element comprising a magnetic male tab extending from the support plate, the magnetic male tab having a disc magnet embedded therein and having a conical lip segment extending over an engagement arc having a sector angle spanning a vertical axis;
    and a wrist strap having a mating engagement element, said wrist strap adapted to be engaged to a wrist of an injured arm, wherein the mating engagement element comprises:
    a magnetic metal disc constrained within a mating modified conical lip segment spanning the vertical axis with a mating engagement arc have a second sector angle less than the sector angle, said mating modified conical lip segment concentrically received over the conical lip segment of the magnetic male tab, whereby engagement of the mating engagement element onto the engagement element adapted to support the injured arm.

2. The arm support system as defined in claim 1, wherein the wrist strap further comprises rotating switch on a dorsal side of the wrist strap, the rotating switch engaged to the magnetic metal disc in the mating engagement magnetic element, located on a palmer side of the wrist strap, to rotate the magnetic metal disc from an attraction orientation to a neutral or repelling orientation with respect to the disc magnet.

3. The arm support system as defined in claim 1, wherein the wrist strap comprises:
    a pliable wrist support element, wherein said mating modified conical lip segment extends through an aperture in the pliable wrist support element; and,
    a pliable wrap adapted to surround the wrist to be engaged to the pliable wrist support element with a hook element of a hook and loop fastener.

4. The arm support system as defined in claim 3 further comprising a bendable spade element carried within the pliable wrist support element.

5. The arm support system as defined in claim 4 wherein the mating modified conical lip segment extends through the aperture from a flange constrained by a circumference of the aperture, the flange having a plurality of protruding tabs which are selectively received in a plurality of mating holes in a base of the bendable spade element.

6. The arm support system as defined in claim 5 wherein selection of clocking of the flange and the plurality of protruding tabs with respect to the plurality of mating holes allows selection of support for a left wrist and arm or a right wrist and arm.

7. The arm support system as defined in claim 6 wherein the magnetic metal disc is constrained in the pliable wrist support element positioned within an inner circumference of the flange for engagement with the disc magnet, said base of the bendable spade element having an oblong aperture with intersecting first circular circumference and second circular circumference with placement of the magnetic metal disc within the first circular circumference with mating modified conical lip segment and flange clocked for left wrist support and within the second circular circumference with mating modified conical lip segment and flange clocked for right wrist support.

8. The arm support system as defined in claim 7 wherein the bendable spade element is deformable and adapted to wrap around the wrist with the pliable wrist support element forming a padded support element adapted to engage an ulnar aspect of the wrist to react weight of the wrist and arm when supported from the mating modified conical lip segment.

9. The arm support system as defined in claim 1, wherein the harness comprises:

a shoulder pad adapted to be received on a trapezius muscle between a neck and deltoid muscle;

an under-arm strap extending from a front lower lateral tab on the shoulder pad under an uninjured am, and adapted to encircle the uninjured arm and engaging a rear lower tab on the shoulder pad;

a chest strap extending from a posterior mid tab on the shoulder pad under an injured arm and adapted to encircle the chest and engaging an anterior lower medial tab on the shoulder pad, the engagement element supported on a bottom tab extending from the shoulder pad acting as the support plate.

* * * * *